United States Patent
Rojas de Naguila

(10) Patent No.: US 9,782,449 B2
(45) Date of Patent: Oct. 10, 2017

(54) METHOD FOR THE TREATMENT OF ADDICTION TO TOBACCO

(75) Inventor: Pabla Beatriz Rojas de Naguila, Montevideo (UY)

(73) Assignee: AMERICAN LIFE NATURALLY, Atlanta, GA (US)

( * ) Notice: Subject to any disclaimer, the term of this patent is extended or adjusted under 35 U.S.C. 154(b) by 852 days.

(21) Appl. No.: 14/234,836

(22) PCT Filed: Jul. 27, 2012

(86) PCT No.: PCT/US2012/048509
§ 371 (c)(1),
(2), (4) Date: Apr. 18, 2014

(87) PCT Pub. No.: WO2013/016621
PCT Pub. Date: Jan. 31, 2013

(65) Prior Publication Data
US 2014/0287073 A1    Sep. 25, 2014

Related U.S. Application Data

(60) Provisional application No. 61/512,080, filed on Jul. 27, 2011.

(51) Int. Cl.
*A61K 36/886* (2006.01)
*A23L 33/00* (2016.01)

(52) U.S. Cl.
CPC ............ *A61K 36/886* (2013.01); *A23L 33/30* (2016.08)

(58) Field of Classification Search
None
See application file for complete search history.

(56) References Cited

U.S. PATENT DOCUMENTS

| | | | |
|---|---|---|---|
| 6,132,754 A | 10/2000 | Hudson | |
| 6,431,874 B1 | 8/2002 | Szynalski | |
| 6,845,777 B2 | 1/2005 | Pera | |
| 2004/0254511 A1 | 12/2004 | Brborich | |
| 2006/0264497 A1 | 11/2006 | Zeligs | |
| 2014/0287073 A1 | 9/2014 | Rojas De Naguila | |

FOREIGN PATENT DOCUMENTS

WO    WO 2013016621    1/2013

OTHER PUBLICATIONS

Fiore, M, et al. Treating Tobacco Use and Dependence: 2008 Update. U.S. Department of Health and Human Services, [retrieved on Oct. 22, 2012]. Retrieved from the Internet: <URL: http://www.publichealth.va.gov/smoking/quit_smoking.asp>, abstract, Figure 1.2; Table 6.8; pp. 6, 11,24,32,65,66, 76,97, 105, 131, 149, 187, 193.
Treatment at Sanoviv. Datasheet [online]. Sanoviv Medical Institute, 2010 [retrieved on Oct. 22, 2012]. Retrieved from the Internet: <URL: http://janmills.net/wp-content/uploads/2010/02/The_Sanoviv_Approach1.pdf>, pp. 14 and 42.
Carpentier, PH, et al. Randomized Trial of Balneotherapy Associated With Patient Education in Patients With Advanced Chronic Venous Insufficiency. From the American Venous Forum [online], Jan. 2009 [retrieved on Oct. 22, 2012], Retrieved from the Internet: <URL: http://www.sciencedirect.com/science/article/pii/S0741521408012822>, Methods and p. 2.
Vetitnev A. M. et al. Kurortnoe delo. Uchebnoe posobie, M., Knorus, 2006 (p. 22, 31, 77).
Khan MA, "Formulation ID: JA7/319A14", TKDL, p. 166, 1887.
Khan MG, "Formulation ID: NA2/275Y", TKDL, p. 666, 1911.

*Primary Examiner* — Susan Hoffman
(74) *Attorney, Agent, or Firm* — Leason Ellis LLP

(57) ABSTRACT

A method for the treatment of addiction to tobacco includes the stages of i) interviewing and training of a tobacco user (patient) and an accompanying person (ii) undergoing a Domiciliary Intensive Detoxification Program, including breathing and corporal exercises, directed balneotherapy, dietary measures including the intake of selected groups of foods and aloe vera gel, hygienic and oral rehabilitation measures and (iii) adhering to a maintenance program.

20 Claims, No Drawings

METHOD FOR THE TREATMENT OF ADDICTION TO TOBACCO

CROSS-REFERENCE TO RELATED APPLICATION

The present application claims priority to U.S. patent application Ser. No. 61/512,080, filed Jul. 27, 2011, which is hereby incorporated by reference in its entirety.

TECHNICAL FIELD

The present invention is relates to a method for helping a person eliminate tobacco dependency, and more particularly pertains to a new and improved method wherein the method includes the steps of conducting an interview or meeting to increase awareness (and assign a composer to assist the tobacco user); undergo a domiciliary intensive detoxification (DID) program; and adhere to a maintenance regimen.

BACKGROUND

A drug can be defined as any substance with a psychoactive effect that is potentially able to produce addiction. A drug addict is periodically or chronically intoxicated, shows a compulsion to take the preferred substance (or substances), has great difficulty in voluntarily ceasing or modifying substance use, and exhibits determination to obtain psychoactive substances by almost any means.

For this reason, some authors define addiction as a disease that has limited neurological location to an area of the human brain named the limbic region, precisely in the brain insula.

Addictive diseases have causal agents so any organism having an addiction has conditioned its response to these repetitive and cumulative agents.

An addiction is considered a disease not only because it has causal agents and it generates consequences for organic impairment, but also because it also goes through the stages of evolution, periodical status, treatment and cure.

On the other hand, addiction is considered a neurological disease because it alters the organic and anatomical central nervous system and the sympathetic nervous system (neurons). Besides, in addition to the neurological injuries, one must add lesions in other organic locations.

The vast majority of people dealing with the use of drugs or that at least discuss drug addiction typically do not include two drugs whose acquisition and use are legalized throughout the world, namely, tobacco and alcohol.

Suffice it to look at what is happening now with the use and abuse of alcohol and that is directly related to traffic accidents, to deaths and mutilations that are a real epidemic in our society. Not including the impact on relations between the addict and his/her family (co-alcoholics) and his/her social environment and workplace.

Moreover, most of those people affected by tobacco are in the productive age, subject to compliance with the working day; and considering the restrictions on smoking in closed public places, the habit of smoking becomes not only a health problem but also a socio-economic one. It is not possible to ignore the importance of passive smokers, especially at home and its impact on their family environment (co-nicotinics).

The use of drugs is directly involved in human behaviors, separating them far from the social coexistence equilibrium. When a smoker is told that he/she is a drug addict, the individual usually gets angry, does not understand it and does not accept it (is in a denial phase).

It is necessary to change the popular point of view that considers that tobacco and alcohol are not drugs, because this misconception makes it very difficult to manage this subject for therapeutic purposes and even more difficult to do it from the social point of view. The reality is that these substances are drugs and can become highly addictive to the user.

The system to approach the disease denominated "smoking" must be addressed in compliance with the definition of the World Health Organization that states: "Smoking is a chronic addictive epidemic disease, with a tendency to relapse."

In the case of smoking, it is recognized that the substances that compose tobacco smoke which is introduced into the respiratory tract and mucosa, enter the bloodstream and circulate around all tissues and fluids of the body, reaching the brain in seven seconds.

The Central Nervous System is one of the regions of the body that shows a greater avidity for nicotine and therefore is one of the most affected by the substances present in cigarette smoke; It has been proved by different studies that the limbic zone of the brain is one of the most affected by nicotine and it is on the brain insula where disorders and alterations in the functionality of neurons have been found.

Neurobiology reports that the limbic area of the human being controls important functions such as the will, feelings and emotions. This means that any person carrying any addiction, in this case a tobacco addict, has these functions altered.

When applying treatments that do not remove these toxic substances introduced into the body in a chronic form in an "intensive" manner, it enables the body to accumulate these substances in different tissues without certain possibilities of spontaneous elimination. These treatments are thus less then entirely effective.

Human tissues exhibit different degrees of affinity to these toxins and therefore have a greater or lesser injury or disturbance due to them. Thus, it is known, for example, the extent to which tar impregnates the periphery of the lungs and placenta.

Smoking is associated not only to the currently recognized damage provoked to the health of smokers (respiratory problems and their impact on ventilation and breathing), but also its relationship with other diseases that appears in the short, medium and long term and that are directly related to toxins present in cigarette smoke has been demonstrated, the most common being nicotinic arteriopathy of carotids, heart, kidneys and lungs.

These major arteries are damaged mainly by nicotine which is recognized for its dynamic action on the circulatory system because its presence changes the tone and arteriolar walls of peripheral circulation, the terminal arterioles of all organs and essentially the vasa vasorum and vasa nervorum that nourish the structures of the great vessels.

This is the main cause of the blockage of large vessels (thrombosis and stroke), mouth sores, cataracts and genetic disorders. Its relation with cancer has been proved.

The introduction of cigarette smoke into the body through the respiratory tract causes immediate irritation and inflammation, as well as an increase of secretions or dryness of mucous membranes depending on the patient, due to the contact of these organic structures with cigarette smoke.

This combustion product acts directly on the respiratory tract causing the stoppage of bronchial cilia; moreover, some components of cigarette smoke contain substances that act on the bronchial wall, i.e., in their anatomical structure.

Nicotine and other components that accompany it have an action on the bronchial tone, acting directly over the smooth fiber which is a part of the bronchial structure and bronchioles.

The permanent harmful action on the light and bronchial walls leads to irreversible bronchiectasis.

When bronchial spasms remain for a while, they generate emphysema, a disease that is characterized because the stale air is trapped in the alveoli, distending and irritating the alveolar wall.

In addition to this situation, there is an altered blood distribution also due to nicotine which acts on the wall of the capillaries that are at the level of the alveoli (nicotinic arteriopathy), which triggers lung emphysema. It is also not possible to hide the interference in the hematosis process.

Moreover, due to inflammation of the bronchial wall and of the bronchioles, smokers develop chronic bronchitis. The spasm and irritation leads to inflammation; the body tries to repair and repair becomes a scar. This process of tissue organization around the inflammation leads to reparative fibrosis, which is the first stage of Chronic Obstructive Pulmonary Disease (COPD).

In the second stage of COPD, there are successive closures of alveoli and bronchioles jeopardizing the fibrotic alveoli, thus affecting the functionality of lung parenchyma, consequently resulting in a decreased lung capacity (smoker's respiratory distress).

In the third stage smokers are exposed to decompensation. They usually visit the doctor when they are in this third stage, especially when an intercurrent complication triggers decompensation.

While in the state of the art is possible to find several smoking cessation treatments, none has the distinctive features of the method discussed herein in accordance with the present invention. Thus, U.S. Pat. No. 6,845,777 of Pera describes a composition to quit smoking that includes the use of tobacco or derivatives, antioxidants, SAMe and caffeine.

U.S. Pat. No. 6,132,754 of Hudson details a method to help the patient to eliminate the dependence on tobacco that includes helping the patient in his/her desire to quit smoking combining the use of medicines and behavior therapy.

U.S. Pat. No. 6,431,874 of Szynalski claims a method for smoking cessation which comprises three steps: (i) educate the smoker in relation to physiological damage and techniques for quitting smoking, (ii) give the smoker a hypnosis program that includes classroom training and the use of prerecorded material and (iii) general dietary substances to improve their nutritional status and substances that help to control withdrawal symptoms and weight gain that occurs as a consequence of abandoning the addiction. Each of the above mentioned U.S. patents is hereby expressly incorporated by reference in its entirety.

While these methods offer some solutions and have some success, there is a need for an improved method that provides improved success and overcomes the deficiencies of the above methods and others.

SUMMARY

A method for the treatment of addiction to tobacco includes the stages of i) interviewing and training of a tobacco user (patient) and an accompanying person (ii) undergoing a Domiciliary Intensive Detoxification Program, including breathing and corporal exercises, directed balneotherapy, dietary measures including the intake of selected groups of foods and aloe vera gel, hygienic and oral rehabilitation measures and (iii) adhering to a maintenance program.

Part of the DID program includes the step of administering an aloe vera gel under conditions of a stabilized suspension and maintaining an established diet and oral hygiene program for a prescribed period of time after the DID program is completed, wherein the administration of aloe vera is continued over the prescribed period of time (e.g., 30 days). In one embodiment, the DID program lasts no more than 14 hours. The dietary measures includes the step of consuming, according to a prescribed schedule, foods containing arginine, ornitine, uronic acids and antioxidant agents, with the foods being selected from the group consisting of: apple, cucumber, carrot, lettuce, radish and turnip, lean meats, eggs and milk and oat.

The DID program further includes the steps of: performing physical breathing exercises and body relaxation exercises, performing directed balneotherapy for the elimination of toxins through the skin and performing hygiene, respiratory and oral rehabilitation. The step of performing directed balneotherapy can include conducting four bathing sessions in which specific stimulating massage, water, vegetable sponge and neutral pH soap are used as part of the directed balneotherapy. At least one of the bathing sessions is performed prior to breakfast and one other is performed at an end of the day prior to bed. Wherein during the DID program, the aloe vera is administered in two intakes, one before eating in early morning and the other before bedtime. The aloe vera suspension is in the form of a dose that is administered and has a volume between about 40 ml and about 100 ml.

In one embodiment, the prescribed period of time for the maintenance is at least 30 days. In addition, during the DID program and the step of maintaining the oral hygiene program, aloe vera toothpaste is used.

DETAILED DESCRIPTION OF CERTAIN EMBODIMENTS

Unlike the abovementioned methods, the treatment for smoking cessation described herein in accordance with one embodiment of the present invention includes a first step of detoxification which instructs the patient and a person chosen by the patient to accompany him/her and assist him/her to meet and conduct treatment indications.

The accompanying person should be a person the patient trusts in, within his/hers affective domain who is trained and instructed for the function that is assigned to him/her during treatment. During application of the method, as described below, the patient is not told to stop smoking and there is no use of techniques to help him/her to quit smoking, the patient decides not to smoke because he/she does not feel the need; as a result of the body being free from toxins that conditioned his/her addiction, the compulsion to smoke disappears. On the other hand, treatment does not use medicines to control withdrawal symptoms because advantageously there are none. The elimination of toxic substances produced in an intensive removal of the causative agents that produce addiction) does not necessitate any other therapeutic measure.

There is no weight gain or substitution of one addiction for another in patients undergoing this treatment, a situation that occurs when tobacco addiction is changed for food addiction. This situation is resolved with nutritional education and begins with the application of the proposed detoxification method.

The inclusion of a detoxification step thus yielded unexpected superior results compared to the previous known methods and eliminates many of the adverse side effects associated with such previous methods. In accordance with the present invention, an unexpected synergistic effect is realized by the inclusion of a detoxification step in a method for treating people who suffer from tobacco addiction or are otherwise adversely affected by tobacco.

The present invention thus consists of a method to treat people affected by tobacco. The person affected by tobacco is the one that suffers from this drug addiction in its various forms (e.g., cigarettes, cigars, snuff or other products that contain tobacco). Treatment of the patient consists of three distinct stages, namely, (i) interview or motivation and awareness meeting, (ii) Domiciliary Intensive Detoxification Program (DID); and (iii) Maintenance.

The First Stage: Interview with Composer and Patient

The first step of treatment, in accordance with one embodiment of the present invention, consists of an interview or meeting of awareness in which the doctor (or teacher, etc.), the patient and his/her composer participate.

As used herein, a "Composer" is the person who is chosen by the patient, to be his/her assistant during the day of the DID. This person assists the patient unconditionally from the moment of the first interview and has a decisive role the day of the DID, as the composer must comply with and enforce all the information related to treatment. This is the reason why the composer has to be trained and motivated to fulfill his/her role.

Both the patient who decides to undergo the treatment at home and the patient who accepts a hospitalization regime must be accompanied by his/her composer.

The main objective of the first interview is to obtain the patient's motivation in order to start detoxification, following the guidelines of the DID and not to abandon treatment.

A commitment is generated between the doctor, patient and composer which is key to achieving a successful treatment. This event is documented in a "Contract" in which the patient makes a real commitment with himself/herself. And this is the first step of the behavior change that is proposed to the patient. The contract thus lists pertinent information regarding the patient's goals and the cessation of smoking and is signed by the patient.

Usually in the first interview there are questions regarding the use of other addictive substances by the patient. The potentially additive substances can be in the form of coffee, alcohol or other stimulants, with the emphasis made on the combination of tobacco and alcohol and the discouraging of consumption of the latter during the DID stage.

During the interview the implications of physical impairments (diseases directly related with the prolonged use of tobacco) and psycho-emotional engagement of the patient caused by the consumption of this drug is explained in simple terms. Then both the patient and composer are instructed on the stages of DID, the latter receiving specific training regarding his/her role in this stage.

The instructions both for the patient and the composer include all the information related to the next stage of treatment and specifically explain the DID program's sub-steps, including specific details of the order and conditions in which activities must be performed (dietary measures, breathing exercises, directed balneotherapy, etc.) as discussed herein.

Contrary to popular belief that smoking relieves stress, it is proven that smoking and stress triggers an increased production of circulating adrenaline. The two stimuli (stress and smoking) are added, even though the smoker has the feeling of relief when consuming tobacco.

The illusion that the patient is handling the stress, based on the soothing action of smoking, is only due to satisfying the need of the addiction. The feeling of wellbeing manifested by the smoker is due to the response of the brain against the supply of substances that decreased their blood concentration. It only meets the exacerbated desire to smoke again, as a result of addictive disease.

The possibility of undergoing the intensive detoxification with the help of the composer, leads to the recovery of the "ego", "self-esteem" and "dignity", of whose loss the patient was unaware. When the patient is asked why does he/she smoke, the most common response is "because it gives me pleasure." During the interview, it is explained to the patient the meaning of immediate pleasure, which in the case of addictions is ephemeral, short lasting and certainly unhealthy, harmful and with a tendency to repeat the habit with increasing frequency.

The interview stage can thus educate the patient regarding smoking, its physiological dangers and its addictive nature as well as other information that is helpful to the patient.

Second Stage—DID Program

Cessation of smoking is not enough to cure the disease of smoking because many toxic substances contained in the smoke of tobacco have biochemical combinations that do not make possible to eliminate them spontaneously. It is not possible or advisable to entrust to time the function of eliminating toxins contained in cigarette smoke that circulate in the blood and accumulate in various organs and tissues. This method tends to treat addictive disease and the risk of recurrence.

The present applicant has thus discovered that the inclusion of a detoxification stage overcomes the deficiencies noted and associated with the prior art methods and provides a superior patient treatment since toxic substances that have collected in the patient's body are addresses and eliminated by treatment.

Detoxification is necessary for regulation of bodily functions that were altered because of smoking without the presence of toxins accumulated over a long time. It is recommended this bone and tissue impregnation be removed as quickly as possible, so as to prevent its action, without forcing the natural mechanisms.

These parameters are fulfilled in the DID stage in accordance with the present invention. The DID stage thus not only improves the patient's health by eliminating these stored up toxins but also in combination with the other steps in the order discussed herein, it has been discovered that this stage provides an improved treatment method for helping a tobacco user stop using tobacco.

The present procedure is preferably performed at patient's home, which needs to be changed in order to act on the impregnations, as a result of the exhalation products of smokers, on objects such as furniture, draperies, curtains and clothing commonly used in homes. However, it is possible to perform DID in a hospitalization regime. In this case, it is necessary to satisfy smoker's needs and to bring the composer he/she has chosen as part of his/her psycho-emotional environment. The environment where the DID is held must be comfortable, friendly, like an extension of his/her own home in order to make the DID process as easy as possible.

The method in accordance with one embodiment of the present invention consists of an ordered sequence of steps whose duration is one day (i.e., less than 24 hours). For example, the DID in accordance with one embodiment lasts about 14 hours (i.e., less than or equal to about 14 hours; and can be between about 12 hrs and 14 hrs, etc. or less in another embodiment), during which the patient with his/her composer passes through different stages that include physical, hygienic, diet and behavior measures.

These measures are aimed at attacking the "causal agent" of the disease by provoking the elimination of the most toxic substances that cause addictive disease. This mechanism of detoxification in a very short time is very important to achieve an intensive elimination. This places the body under favorable conditions to recover the normalization of nutritional status, metabolism and internal conditions to prevent relapses.

Most known treatments use alternative substances primarily for managing withdrawal symptoms, however when applying the DID in accordance with the present invention, it is not necessary to use any substitution substance (i.e. drugs) in treatment of the patient.

Toxins responsible for addictive disease (smoking) are eliminated through the natural emunctories: skin, kidneys and lungs. For this reason, natural emunctories are used during the DID in order to eliminate in the shortest time possible the toxic substances which trigger the mechanism of addiction.

In accordance with the present invention, part of the DID stage includes a modification of the daily diet of the patient. In particular and as set forth below, the DID stage involves monitoring and modification of the patient's diet in order to promote the detoxification of the body, and thereby provide the improved method of treatment when combined with the other steps described herein.

Dietary Measures

Dietary measures are implemented on schedule and involve the intake of foods with recognized nutritional and anti toxic properties. The diet is tailored to the actual deficiencies that smokers carry due to enzymatic processes caused by the interference of toxic substances introduced by smoking habit (e.g. nicotine's interference in the metabolism of vitamin D that prevents the binding of calcium to the bones, or the direct action on the metabolism of vitamin C, consuming the reserves with only smoking 4 cigarettes a day). In other words, the smoking directly impairs the body's use of vitamin D and C and therefore, the modified dietary measures take this into account and supplements for deficiencies. This improves profits after detoxification, because there are no substances that are competing in the proper use of vitamins, minerals and trace elements.

A balanced diet with a sequence that takes into account precisely not to incur in imbalances such as hypoglycemia, compensates nutritional gaps of smokers providing selected food in quality and quantity.

The DID also includes a healthy sequence of meals (four meals), respecting the hours for the same, the quantity and quality of nutrients. The monitoring of the compliance with these conditions during the DID is the composer's responsibility.

Based on the foregoing and according to the DID, the patient's diet is structured to include the following foods and in particular, foods that are selected for antitoxic nutritious diet include the following:

Apple: contains sodium, potassium, magnesium, phosphorus, iron, malic acid, citric acid, cystine and arginine, the latter together with the malic acid are involved in detoxification processes, and have diuretic action. The antioxidants help to neutralize free radicals.

Orange: contains plenty of vitamin C and B complex (B1, B2, B3, B6 and B12).

Carrot: contains the precursor of vitamin A, B1 and vitamin C, plus potassium, sodium, iron, phosphorus and calcium. It has detoxifying and antioxidant action and has minerals and trace elements.

Cucumber: is a natural diuretic and its components are involved in the immune processes. It contains potassium, phosphorus, magnesium, B complex and vitamin C.

Lettuce: has diuretic and sedative action and contains Lactusina, Lactacerol, lactide acid.

Radishes and turnip: are involved in the synthesis of genetic material and the formation of antibodies. They also have diuretic action. They contain vitamin C, potassium, iodine, calcium, magnesium, zinc and sulfur (antioxidant).

Eggs and dairy products with oat, provide tryptophan.

In each meal, a list of foods that can be combined is indicated with a sequence that must not be altered in order to get the patient accustomed to the discipline.

Some foods are used due to their specific antitoxic, diuretic, restorative, sedative, antioxidant and stimulating of the immune processes actions.

The proteins are added at breakfast, lunch and dinner and in the case of meat intake, it is recommended to be lean. Essential amino acids are introduced into the scheduled intake of aloe vera.

Is important to note that the intake of juices made from selected fruits and vegetables is one of the decisive factors involved in the intensive detoxification; These juices must be in the gel state to ensure their passage to the blood in the shortest time as possible and to get the electrolyte exchange mechanism that will enable the elimination of toxins through renal excretion. During the DID day between 5 and 11 liters of liquids are introduced into the body in various forms (broth, juice, tea, whole fruit) the optimum quantity being 9 liters; however, this depends in part upon the specifics of the patient, including the patient's weight, etc.

Thus, the amount of fluid taken and the diuretic effects of some of the selected fruits and vegetables, stimulates diuresis during the DID Immediate consumption of juices is emphasized in order to prevent oxidation and/or the loss of labile components and antioxidants needed during the intensive detoxification process.

Administration of a Gel

In accordance with the present invention, the present Applicant has discovered that the application of aloe vera in combination and as part of the present detoxification plan yields a surprising synergistic effect that results in an improved treatment and greater success.

In particular, aloe vera is administered under conditions of stabilized suspension, in its commercial use presentations. In particular, the aloe vera can be suspended in a solution (e.g., water or other drinkable liquid). During the DID, there are two intakes of this natural product, before eating in the early morning and before bedtime. The dose to be administered varies between 40 and 100 mL.

Aloe vera acts as a nutrient and restorative of altered metabolic processes, given its composition of vitamins and minerals, trace elements and essential amino acids and contains the three antitoxins required for the DID: ornithine, arginine and uronic acids, whose presence allows the faster elimination of toxins that are present in fluids and tissues of smokers.

The contribution of Arginine, Ornithine and uronic acids present in this nutritional supplement that is indicated and described above is extremely important because a single food combines these three substances in a natural, antitoxic way and the body is able to fully use them; Aloe Vera gel is an important adjuvant to the process of elimination within hours of the causal agents of this addictive disease. Aloe Vera also helps to fight free radicals that damage cells.

Physical Breathing Exercises and Body Relaxation

During DID special attention is paid to the respiratory tract from the nose to the alveoli, as it is the most common route of entry for the smoke and can be subject to further damage and chronic irritation. Based on breathing exercises with controlled time and frequency of inhalation and exhalation ventilation is regulated and therefore breathing as well.

The exercises consist of conscious inhalations and exhalations inducing the patient to recognize his/her own breath. This is one of the most important functions for maintaining biological processes essential for life (external breath). It is necessary to take into account the frequency of performance of breathing exercises during the DID and the indications to get the movement and tone of the diaphragm and inter-ribcage muscles.

The tone and movement of the diaphragm is achieved using an appropriate weight on the abdomen in supine position, regulating the inspiration and forced expiration. The chest expansion is stimulated by acting on the inter-ribcage muscles and by prolonged exhalations the patient is taught to mobilize the residual air present in his/her lungs. Thus, mobilization and adequate expansion of the chest cavity, mobilization of bronchial secretions and removal of residual air, which in smokers is always flawed because of emphysema, are stimulated.

These breathing exercises are performed with the active intervention of the composer, who accompanies the patient in order to help him I her reach a conscious breathing rhythm.

Both the relaxation and the flotation exercise are added to help to manage the cravings that can appear in the early hours of the application of the DID and the patient is advised to perform them any time he/she feels overwhelmed by stress. A Relaxation Exercise applied for 15 minutes twice a day helps to calm the patient through tensing and relaxing different parts of his/her body, accompanied by breathing.

Flotation exercise allows the patient sitting in a comfortable position for him/her to relax and feel light, through movements performed with the body from head to toes. This exercise removes patient's anxiety, nervousness and present or potential fears.

Directed Balneotherapy

In accordance with the present invention, the DID program includes directed balneotherapy. This procedure is conducted by the composer and is intended firstly as a mechanical drag on the toxins, which are eliminated through the skin by means of massage and frictions in specific areas of the body and secondly, provide the patient with emotional support sustained by verbal communication that the composer must maintain with the patient.

During the bathing sessions, the composer massages the patient to stimulate brachial, cervical, thoracolumbar, groin and lower limb plexus, in order to achieve greater flow of blood in the peripheral circulation and a greater extent of removal of toxins through the skin. Water, neutral pH soap and vegetable sponge meet the conditions required to achieve this goal.

It is recommended that this procedure is repeated for at least four sessions the day of the DID, it being essential to perform the first one of them before breakfast and the other at the end of the day.

Hygiene and Oral Rehabilitation

From the day of the DID and during subsequent maintenance, aloe vera toothpaste is used in order to: a) enable and maintain oral hygiene; b) change the pH of the smoker's mouth; c) stimulate the sense of taste and to act on the oral cavity (gateway to cigarette smoke); d) improve the arteriopathy of the gums by massaging them, and in the oral cavity with the toothpaste for the purpose of improving chronic congestion caused by nicotinic arteriopathy.

Once again, the present applicant discovered the benefits obtained by the incorporation of aloe vera Third Stage—Maintenance At the end of DID stage, clear indications on how to proceed with the subsequent rehabilitation are given to the patient. It is suggested to the patient that the patient visit a dentist to proceed with the rehabilitation of the smoker's mouth and visit a pulmonologist to determine in which stage of COPD he/she is, so as to take appropriate measures for pulmonary rehabilitation and prevent the progression of this disease.

Diet, oral hygiene and the administration of aloe vera gel should be kept up for at least 1 month (e.g., at least about 30 days) after the DID stage ends (in one embodiment this regimen is maintained for at least 45 days and in another embodiment, for at least 60 days). This ensures that toxins are removed from the body.

The claimed method ensures the elimination of toxins through the three natural emunctories carried out in fast, safe, natural, and comfortable conditions and with no side effects.

No less important is the fact that withdrawal syndrome, as feared by patients who smoke, does not appear when the method of the present invention is undertaken. This is an unexpected benefit of the incorporation of the DID stage into the patient's treatment and by maintaining certain elements during the maintenance stage as discussed.

Another important novelty of the proposed method is the active intervention of a customized participant chosen by the patient within his/her affective sphere, the composer, who acts on patient's psychosomatic field to help in the affective behavioral recovery.

It should be noted that the method herein described disregards the introduction of drugs, using known organic substances and authorized by the Health Authorities, which use is not far from the normal diet, but foods to be consumed are selected by their nutritional, antitoxic, sedative, diuretic and antioxidant properties.

The causal agents are removed from the bloodstream, tissues and fluids and are excreted through the natural emunctories.

The method informs, educates and teaches the patient to consume foods with adequate quality and quantity, with the aim of a nutritional re education, detoxifying and nourishing that regulates and maintains metabolism after detoxification, helping to avoid the replacement of one addiction for another (food). It provides better prospects for avoiding relapses and intensive release of toxins, which allows cells to regulate their internal metabolism and specially the affected neurons metabolism.

The novelty of this method for the treatment of addiction to tobacco compared to prior art is the sum of new procedures and the practices described herein. Such combination produces a synergistic effect that results in the cure of the addictive disease called smoking.

The present invention can thus be thought of as being directed to a method for helping a tobacco smoker (human) to stop smoking. In other words, it is directed to a method of helping a patient (human) eliminate tobacco dependency.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A method for treatment of tobacco addiction in a tobacco user comprising the steps of:
    conducting an interview with the tobacco user to educate the tobacco user on disadvantages of smoking and its harmful effects, wherein the interview is conducted in the presence of a composer:
    implementing a domiciliary intensive detoxification (DID) program that lasts no more than 24 hours for removing toxins from the tobacco user's body, wherein the DID program includes adhering to prescribed dietary measures, wherein part of the DID program includes the step of administering an aloe vera based drinkable solution that includes natural aloe vera suspended in the drinkable solution, wherein the DID program is monitored by the composer; and
    maintaining a predetermined diet program, that includes a list of foods for consumption with each meal, and an oral hygiene program that includes use of an aloe vera based toothpaste for a prescribed period of time after the DID program is completed, wherein the administration of aloe vera based drinkable solution is continued over the prescribed period of time.

2. The method of claim 1, wherein prior to the step of conducting the interview, the composer is selected and comprises a person who assists the tobacco user during the DID program.

3. The method of claim 1, wherein the DID program lasts no more than 14 hours.

4. The method of claim 1, wherein the dietary measures includes the step of consuming, according to a prescribed schedule, foods containing arginine, ornithine, uronic acids and antioxidant agents.

5. The method of claim 4, wherein the foods are selected from the group consisting of: apple, cucumber, carrot, lettuce, radish, turnip, lean meats, eggs, milk and oat.

6. The method of claim 1, wherein the DID program further includes the steps of: performing physical breathing exercises and body relaxation exercises, performing balneotherapy for the elimination of toxins through the skin and performing hygiene, respiratory and oral rehabilitation.

7. The method of claim 6, wherein the step of performing balneotherapy comprises conducting four bathing sessions in which stimulating massage, water, vegetable sponge and neutral pH soap are used as part of the balneotherapy.

8. The method of claim 7, wherein at least one of the bathing sessions is performed prior to breakfast and one other is performed at an end of the day prior to bed.

9. The method of claim 1, wherein during the DID program, the aloe vera based drinkable solution is orally administered in two intakes, one before eating breakfast and the other before bedtime.

10. The method of claim 1, wherein the aloe vera based drinkable solution comprises a dose that is administered and has a volume between about 40 ml and about 100 ml.

11. The method of claim 1, wherein the prescribed period of time is at least 30 days.

12. The method of claim 1, wherein during the DID program and the step of maintaining the oral hygiene program, aloe vera toothpaste is used.

13. The method of claim 1, wherein during the DID program, between about 5 liters and about 11 liters of liquids are introduced into a body of the tobacco user.

14. A method for helping a tobacco user stop using tobacco products without experiencing withdrawal symptoms comprising the steps of:
    conducting an interview with the tobacco user to educate the tobacco user on disadvantages of smoking and its harmful effects, wherein the interview is conducted in the presence of a composer;
    implementing a domiciliary intensive detoxification (DID) program that lasts no more than 24 hours for removing toxins from the tobacco user's body, wherein the DID program includes adhering to prescribed dietary measures including administering anti-oxidant foods, wherein part of the DID program includes the step of administering at least twice an aloe vera based drinkable solution that includes natural aloe vera suspended in the drinkable solution, wherein the DID program also includes performing balneotherapy for the elimination of toxins through the skin, wherein the DID program is monitored by the composer; and
    maintaining a predetermined diet program, that includes a list of foods for consumption with each meal, and an oral hygiene program that includes use of an aloe vera based toothpaste for at least 30 days after the DID program is completed, wherein the administration of aloe vera is continued over the 30 days and includes administration of the aloe vera based drinkable solution and use of the aloe vera based toothpaste.

15. The method of claim 14, wherein the DID program lasts no more than 14 hours.

16. The method of claim 14, wherein the dietary measures includes the step of consuming, according to a prescribed schedule, foods containing arginine, ornithine, uronic acids and antioxidant agents.

17. The method of claim 16, wherein the diet program includes a structured diet comprising meals that include: apple, cucumber, carrot, lettuce, radish, turnip, eggs, milk and oat.

18. The method of claim 14, wherein the DID program further includes the steps of: performing physical breathing exercises and body relaxation exercises and performing hygiene, respiratory and oral rehabilitation.

19. The method of claim 14, wherein the step of performing balneotherapy comprises conducing four bathing sessions in which stimulating massage, water, vegetable sponge and neutral pH soap are used as part of the balneotherapy.

20. The method of claim 14, wherein during the DID program, the aloe vera based drinkable solution is orally administered in two intake doses, one before eating breakfast and the other before bedtime, wherein each intake dose that is administered has a volume between about 40 ml and about 100 ml.

* * * * *